(12) United States Patent
Sone et al.

(10) Patent No.: US 7,402,727 B2
(45) Date of Patent: Jul. 22, 2008

(54) NON-HUMAN ANIMAL EXHIBITING BONE METASTASIS OF TUMOR CELLS

(75) Inventors: Saburo Sone, Tokushima (JP); Toyokazu Miki, Tokushima (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 15 days.

(21) Appl. No.: 11/120,508

(22) Filed: May 2, 2005

(65) Prior Publication Data

US 2006/0179494 A1    Aug. 10, 2006

Related U.S. Application Data

(63) Continuation of application No. 09/864,364, filed on May 25, 2001, now abandoned.

(30) Foreign Application Priority Data

May 10, 2001    (JP)    ............... 2001-140538

(51) Int. Cl.
*A01K 67/00*    (2006.01)
*A61K 49/00*    (2006.01)
(52) U.S. Cl. ................... 800/10; 800/8; 800/9; 424/9.2
(58) Field of Classification Search ........................ None
See application file for complete search history.

(56) References Cited

U.S. PATENT DOCUMENTS

| | | | |
|---|---|---|---|
| 5,643,551 A | 7/1997 | Namikawa et al. | |
| 5,928,641 A | 7/1999 | Seon | |
| 5,993,817 A | 11/1999 | Yoneda et al. | |
| 6,365,797 B1 | 4/2002 | Sawyers et al. | |
| 7,135,609 B2 * | 11/2006 | Sone ........................... | 800/13 |

OTHER PUBLICATIONS

Arguello et al., *Cancer Res.* 48:6876-6881 (1988).
Blomme et al., *Prostate* 39:187-197 (1999).
Dougherty et al., *Cancer Res.* 59:6015-6022 (1999).
Engebraaten et al., *Int. J. Cancer* 82:219-225 (1999).
Faguet et al., *Blood* 71:1511-1517 (1988).
Faguet et al., *Blood* 71:422-429 (1988).
Fodstad et al., *J. Cell Biochem.* 56:23-28 (1994).
Gresser et al., *Int. J. Cancer* 63:726-731 (1995).
Guise et al., *J. Bone Min. Res.* 9:S128 (1994).
Hall et al., *J. Bone Miner. Res.* 9:221-230, (1994).
Hanibuchi et al., *Int. J. Cancer* 78:480-485 (1998).
Iguchi et al. *Cancer Res.* 56:4040-4043 (1996).
Ishigaki et al., *Folia Microbiol.* 43:493-494 (1998).
Jamasbi et al., *Br. J. Cancer* 36:723-729 (1977).
Kaufman et al., *Annu Rev. Immunol.* 13:339-367 (1995).
Lelekakis et al., *Clin. Exp. Metastasis* 17:163-170 (1999).
Mehta et al., *Breast Cancer Res. and Treat.* 25:65-71 (1993).
Mickey et al., *Int. J. Immunopharmac.* 11:829-838 (1989).
Miki et al., *Oncol. Res.* 12:209-217 (2000).
Miki et al., 9th Meeting of the Japanese Association for Metastasis Research (JAMR), Third Department of Internal Medicine, University of Tokushima, Jun. 29-30, 2000, p. 55.
Mule et al., *J. Immunother.* 12:196-198 (1992).
Mundy et al., *Seminars in Oncology* 28(2) Suppl. 6:35-44 (2001).
Nakai et al., *Cancer Res.* 52:5395-5399 (1992).
Niederkorn et al., *Inv. Ophthal. Vis. Science* 27:1355-1361 (1986).
Rabbani et al., *Int. J. Cancer* 80:257-264 (1999).
Sasaki et al., *Cancer Res.* 55:3551-3557 (1995).
Shevrin et al., *Prostate* 19:149-154 (1991).
Turner et al., *J. Neuro-Oncol.* 8:121-132 (1990).
Yano et al., *Int. J. Cancer* 67:211-217 (1996).
Yoneda et al., *J. Bone Miner Res.* 16:1486-1495 (2001).
Office Action in U.S. Appl. No. 09/864,364, mailed on Jan. 16, 2002.
Response filed in U.S. Appl. No. 09/864,364, on Jul. 15, 2002.
Office Action in U.S. Appl. No. 09/864,364, mailed on Oct. 23, 2002.
Response filed in U.S. Appl. No. 09/864,364, on Mar. 21, 2003.
Office Action in U.S. Appl. No. 09/864,364, mailed on Jun. 3, 2003.
Response filed in U.S. Appl. No. 09/864,364, on Dec. 1, 2003.
Office Action in U.S. Appl. No. 09/864,364, mailed on Feb. 25, 2004.
Response filed in U.S. Appl. No. 09/864,364, on Aug. 11, 2004.
Office Action in U.S. Appl. No. 09/864,364, mailed on Nov. 2, 2004.
Office Action in U.S. Appl. No. 10/143,364, mailed on Oct. 6, 2004.
Response filed in U.S. Appl. No. 10/143,364, on Apr. 6, 2005.
Office Action in U.S. Appl. No. 10/143,364, mailed on Jun. 20, 2005.
Response filed in U.S. Appl. No. 10/143,364, on Dec. 19, 2005.
Notice of Allowance, Notice of Allowability, Examiner's Amendment, and Examiner-Initiated Interview Summary in U.S. Appl. No. 10/143,364, mailed on Feb. 2, 2006.
U.S. Appl. No. 11/439,603, as filed May 23, 2006.
Preliminary Amendment filed in U.S. Appl. No. 11/439,603 on May 23, 2006.

* cited by examiner

*Primary Examiner*—Q. Janice Li
(74) *Attorney, Agent, or Firm*—Oblon, Spivak, McClelland, Maier & Neustadt, P.C.

(57) ABSTRACT

The present invention provides a non-human bone metastasis model animal in which tumor cells capable of inducing bone metastasis by peripheral administration have been introduced, and a method for producing the animal.

The bone metastasis model animal in the present invention may be useful for understanding the biology of bone metastasis and developing novel therapeutic strategies for lung cancer patient with multi-organ metastases, including bone metastasis.

13 Claims, 3 Drawing Sheets

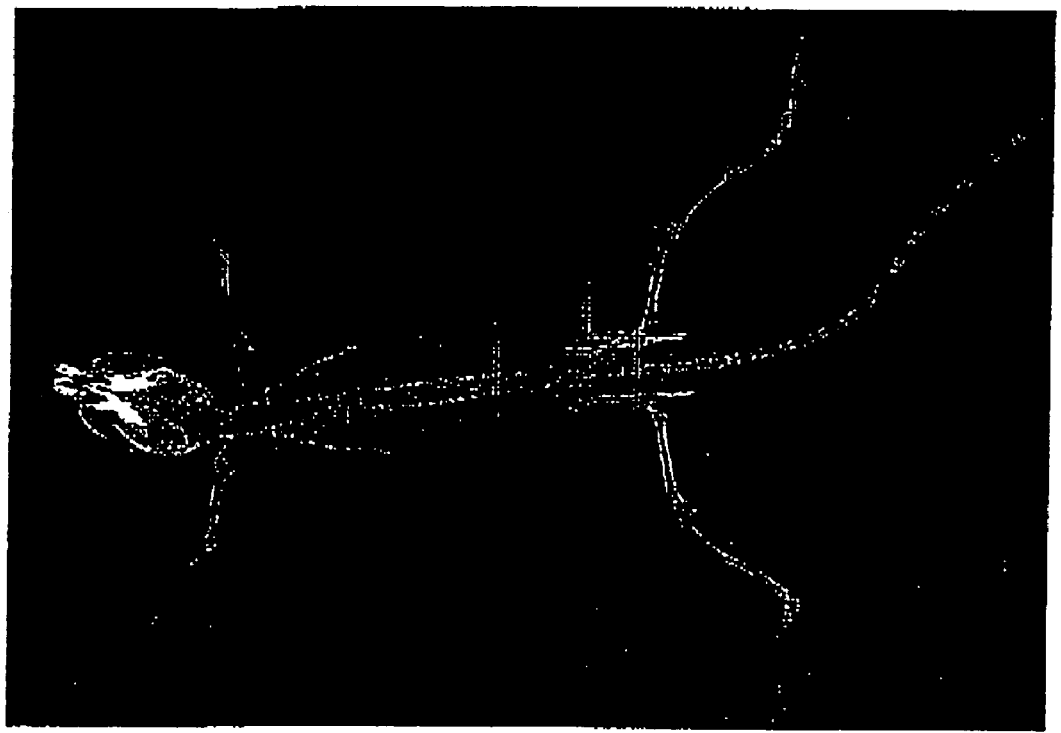
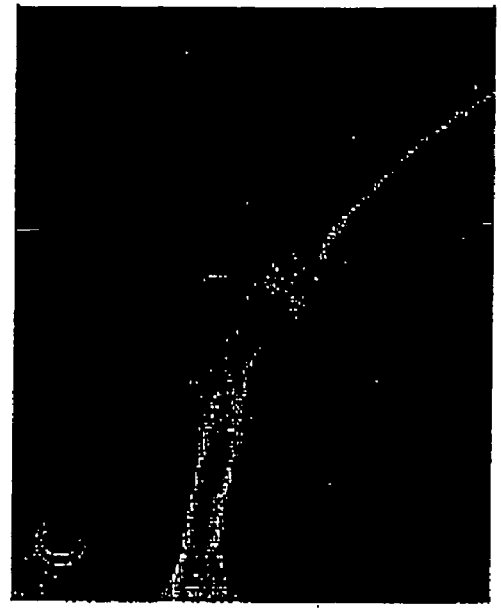

FIG.3
|  | SBC-5 | SBC-3 | SBC-3/ADM | H69 | H69/VP | PC-14 | A549 | RERF-LC-AI |
PTHrP 548b.p. → 
IL-11 322b.p. → 
β-actin 218b.p. →

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PTHrP primer

<400> SEQUENCE: 1

-continued

```
atgcagcgga gagactggtt cag                                          23

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: PTHrP
      primer

<400> SEQUENCE: 2
tcaatgcctc cgtgaatcga gctccagagc cgt                               33

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: IL-11
      primer

<400> SEQUENCE: 3
actgctgctg ctgaagactc ggctgtga                                     28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: IL-11
      primer

<400> SEQUENCE: 4
atggggaaga gccagggcag aagtctgt                                     28
```

NON-HUMAN ANIMAL EXHIBITING BONE METASTASIS OF TUMOR CELLS

This is a continuation of U.S. patent application Ser. No. 09/864,364, filed May 25, 2001, now abandoned, which claims the benefit of Japanese Application No. 2001-140538, filed on May 10, 2001, both of which are incorporated herein by reference.

FIELD OF THE INVENTION

The present invention relates to a non-human animal exhibiting bone metastasis of tumor cells and a method for producing the animal. Specifically, the present invention relates to the animal in which tumor cells capable of inducing bone metastasis by peripheral administration have been introduced, and a method for producing the animal.

BACKGROUND OF THE INVENTION

Lung cancer is an increasingly common cause of cancer-related death in the world, and over 90% of deaths from lung cancer can be attributed to metastasis (Yano, S. et al., Int. J. Cancer 67:211-217, 1996). Lung cancer is histologically classified into two groups, small cell carcinoma (SCLC) and non-small cell carcinoma (NSCLC), based on different clinical behavior (the rate of tumor growth, the pattern of tumor progression, the sensitivity to chemo- and radiotherapy). In both type, however, metastasis to the multiple organs are frequently observed at the time of the diagnosis. Bone, following the liver and brain, is the third most common organs of metastasis in lung cancer patients. In particular, bone metastasis causes various severe symptoms by inducing pathological fracture, compression of spinal cord, and hypercalcemia, and reduces the quality of life of the patients (Iguchi, H. et al., Cancer Res. 56:4040-4043, 1996). Though palliative radiotherapy is given to reduce the symptoms for patients with bone metastasis, novel therapeutic modality is necessary for these patients to improve their prognosis.

Recently much attention has been paid to develop bone metastasis model with human cancer cells in order to understand the molecular mechanism and to develop therapeutic modality. When cancer cells were injected through the intracardiac route in immunodeficient mice, melanoma (Arguello, F. et al., Cancer Res. 48:6876-6881, 1988; Nakai, M. et al., Cancer Res. 52:5395-5399, 1988), breast cancer (Hall, D. G. and Stocia, G., J. Bone Miner. Res. 9:221-230, 1994; Sasaki, A. et al., Cancer Res. 55:3551-3557, 1995), prostate cancer (Shevrin, D. H. et al., Prostate 19:149-154, 1991), and lung cancer (Iguchi, H. et al., Cancer Res. 56:4040-4043, 1996) have been reported to produce bone metastasis.

In these models, tumor cells were inoculated into left ventricle of the heart and bone metastasis was developed in 75% recipient mice. However, intracardiac inoculation of tumor cells does not seem to be technically easy, and is associated with sudden death to some extent. Therefore, intracardiac injection of tumor cells imposes a lot of burden on animals, causing an ethical and economic problems.

SUMMARY OF THE INVENTION

We have succeeded in producing a bone metastasis model animal, which can be used in order to elucidate a mechanism of bone metastasis of tumor cells and develop a useful agents for treating and preventing bone metastasis, by peripheral administration of tumor cells.

We examined the abilities of 8 human lung cancer cell lines injected intravenously into natural killer (NK)-cell depleted SCID (severe combined immunodeficient) mice to generate metastatic nodules in bone and multiorgans, and explored the correlation of parathyroid hormone related protein (PTHrP) to the bone metastasis. Though all the cell lines of small cell carcinoma (SBC-5, SBC-3, SBC-3/ADM, H69, H69/VP) formed metastatic nodules in multiple organs (liver, kidney, and lymph nodes), only SBC-5 cells reproducibly developed bone metastases. Squamous cell carcinoma (RERF-LC-AI) cells metastasized mainly into the liver and kidneys, whereas adenocarcinoma (PC14, A549) produced colonies mainly in the lungs. As assessed by X-ray photography, osteolytic bone metastases produced by SBC-5 cells were detected as early as on day 28, and all recipient mice developed bone metastasis by day 35. The expression of PTHrP in 8 cell lines directly correlated with the formation of bone metastasis. No correlation was observed between the formation of bone metastasis and expression other metastasis-related cytokines (IL-1, IL-6, IL-8, IL-10, IL-11, TNF-α, VEGF, M-CSF). Consistent with the formation of bone metastasis by SBC-5 cells, the levels of PTHrP and calcium in the mouse serum were increased in a time-dependent manner, suggesting that PTHrP produced by human lung cancer may play a crucial role in the formation of bone metastasis and hypercalcemia. These results indicate that bone metastasis model of SBC-5 cells may be useful for clarifying the molecular aspects of metastatic process under the different organ microenvironments and developing therapeutic modalities for lung cancer patients with bone metastases.

Therefore, the present invention provides the following (1) to (25):

(1) A non-human bone metastasis model animal exhibiting bone metastasis of tumor cells, in which tumor cells capable of inducing bone metastasis have been introduced by peripheral administration.

(2) The non-human bone metastasis model animal according to (1), wherein the tumor cells are human lung cancer or breast cancer derived cells highly expressing PTHrP.

(3) The non-human bone metastasis model animal according to (1), wherein the tumor cells are cells from human lung cancer small cell carcinoma.

(4) The non-human bone metastasis model animal according to (1), which exhibits multi-organ metastasis of tumor cells.

(5) The non-human bone metastasis model animal according to (1), wherein the multi-organ metastases include metastases to one or more organs selected from the group consisting of lung, liver, kidney, and lymph node.

(6) The non-human bone metastasis model animal according to (1), wherein the animal belongs to rodents.

(7) The non-human bone metastasis model animal according to (6), wherein the animal is mouse.

(8) The non-human bone metastasis model animal according to (7), wherein the animal is immunodeficient mouse.

(9) The non-human bone metastasis model animal according to (8), wherein the animal is SCID mouse.

(10) A method for producing a non-human animal exhibiting bone metastasis of tumor cells, comprising the steps of:
(i) providing a nonhuman animal having reduced immunity; and
(ii) introducing tumor cells capable of inducing bone metastasis into the animal by peripheral administration.

(11) The method according to (10), wherein the tumor cells are human lung cancer- or breast cancer-derived cells highly expressing PTHrP.

(12) The method according to (10), wherein the tumor cells are human lung small cell carcinoma.

(13) The method according to (10), wherein the step of providing a non-human animal having reduced immunity includes a step of inactivating NK cells in the animal.

(14) The method according to (10), wherein the step of providing a non-human animal having reduced immunity includes a step of reducing the number of NK cells in the animal.

(15) The method according to (10), wherein the step of providing a non-human animal having reduced immunity includes a step of depleting NK cells in the animal.

(16) The method according to (10), wherein the step of providing a non-human animal having reduced immunity includes a step of administering anti-IL-2 receptor antibody to the animal.

(17) The method according to (16), wherein the antibody is anti-IL-2 receptor β-chain antibody.

(18) The method according to (16), wherein the antibody is mouse antibody.

(19) The method according to (10), wherein the step of introducing tumor cells capable of inducing bone metastasis to the animal by peripheral administration includes a step of injecting the tumor cells into the animal intravenously.

(20) The method according to (10), wherein the animal belongs to rodents.

(21) The method according to (10), wherein the animal is mouse.

(22) The method according to (21), wherein the animal is an immunodeficient mouse.

(23) The method according to (21), wherein is SCID mouse.

(24) A method for evaluating efficiencies of treatment against bone metastasis of tumor cells, comprising the step of:
  (i) applying a treatment to the non-human bone metastasis model animal according to any one of (1) to (9); and
  (ii) comparing the size and/or extent of bone metastasis, and/or symptoms resulted from bone metastasis, with control animal.

(25) Use of the non-human bone metastasis model animal according to claim to any one of (1) to (9) for determining the effect of a test substance on bone metastasis, comprising the steps of:
  (i) administering the test substance to the animal; and
  (ii) comparing the size and/or extent of bone metastasis, and/or symptoms resulted from bone metastasis, with control animal.

BRIEF DESCRIPTION OF THE DRAWINGS

FIG. 1 shows X-ray photograph of bone metastasis model mouse of the present invention. 1A indicates osteolytic bone metastases induced mainly in the spine (1B) and bone of extremities (1C).

FIG. 3 shows mRNA expression of PTHrP and IL-11 in various tumor cells.

DETAILED DESCRIPTION OF THE INVENTION

Figure 2A:
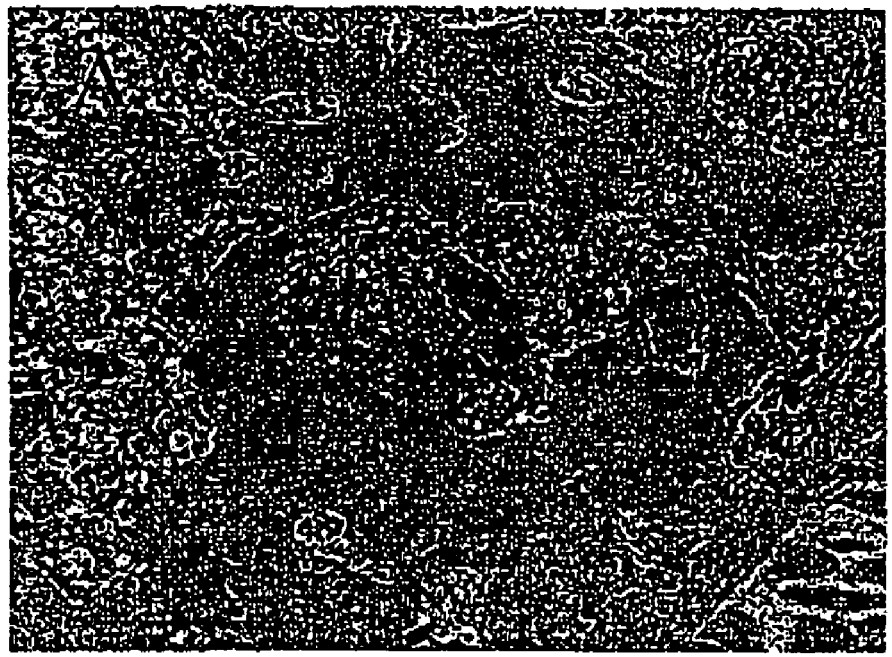
FIG. 2 shows histological analysis of bone metastasis. Bone metastatic lesions consist of tumor cells with multinucleated cells (2A and B).
Figure 2B:
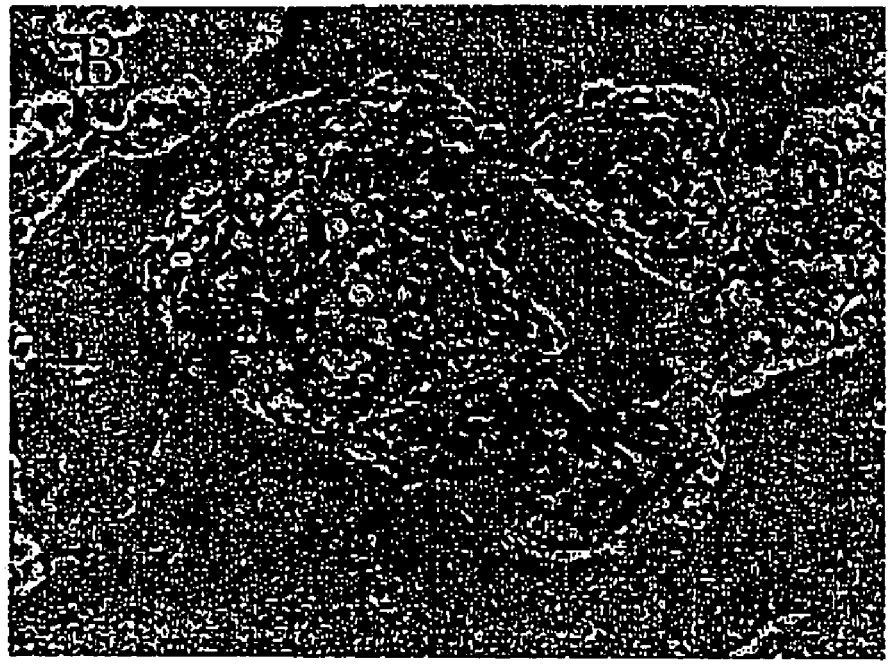

Formation of bone metastasis has been reported to involve various soluble mediators such as cytokines and parathyroid hormone related protein (PTHrP), which was originally identified as a 17 kDa PTH-like adenylate cyclase-stimulating protein from a tumor associated with humoral hypercalcemia of malignancy (HHM)(Suva, L. J. et al., Science 237:893-896, 1987; Broadus, A. E. et al., N. Engl. J. Med. 319:55663, 1988). Interestingly, a variety of tumor cells, including breast cancer, prostate cancer and lung cancer overexpress PTHrP (Burtis, W. J. et al, N. Engl. J. Med. 322:1106-12, 1990). Recently, a highly bone metastatic lung cancer cell line was found to overexpress PTHrP, and that treatment of nude mice with anti-PTHrP antibody inhibited the formation of bone metastasis (Iguchi, H. et al., Cancer Res. 56:40404043, 1996), suggesting that PTHrP plays a critical role in the formation of bone metastasis from human lung cancer.

Recently we showed that depletion of NK cells by anti-IL-2 receptor β-chain antibody TMβ1) in SCID mice resulted in formation of multi-organ metastasis (lung, liver, kidney and lymph nodes) induced by intravenous injections of various human lung cancer cell lines (Yano S., 2 papers). Since there is no reports about evidences showing ability of cancer cells injected intravenously into tail to form bone metastasis in solid tumor other than those of haemal system, we examined whether bone metastasis could be produced by 8 different cell lines of human lung cancer inoculated intravenously in NK-cell depleted SCID mice. Moreover, we also evaluated the correlation of the expression of PTHrP and cytokines with the formation of bone metastasis in human lung cancer cell lines.

The bone metastasis model animal of the present invention refers to a non-human animal exhibiting bone metastasis of tumor cells. In the present invention, the phrase "exhibiting bone metastasis of tumor cells" means the animal carries one or more bone metastasis originated from tumor cells which has been introduced by peripheral administration. Animals which carries metastasis to other organs such as lung, liver, kidney, lymph node together with bone metastasis are also included. In the case of such multi-organ metastasis, effectiveness of the same agents for bone metastasis and metastasis to other organs can be examined simultaneously. Although the existence and degrees of bone metastasis in non-human animal can be detected as a image of bone absorption (punch-out image) with X-ray photography and/or identify by means of histological analysis, the means of identification of bone metastasis is not particularly restricted.

Tumor cells which can be used in the present invention are capable of inducing bone metastasis by peripheral administration and include, for example, lung cancer such as squamous cell carcinoma, small cell carcinoma, adenocarcinoma, large cell carcinoma, adenosquamous carcinoma, carcinoid tumor; breast cancer such as noninfiltrating carcinoma, invasive carcinoma (invasive galactophore carcinoma, mucus carcinoma, invasive lobular carcinoma, squamous cell carcinoma and the like); and other cancers such as kidney cancer, prostate cancer, stomach cancer, liver cancer, intestinal cancer, pancreas cancer. Tumor cells are preferably those highly expressing PTHrP. The term "highly expressing" means herein that PTHrP can be detected at a certain concentration or higher in cell culture supernatant, in particular, in the case of measuring PTHrP C-terminus, that PTHrP can be detected in the concentration higher than that detected in normal individuals. The above term also means that PTHrP can be detected at a certain concentration or higher in blood of non-human animals such as a nude mouse which is implanted with the tumor. For example, the cases where 1.1 pmol/L or higher PTHrP is detected in measuring PTHrP-N terminus (for example, Mitsubishi kagaku Bio-chemical Laboratory Inc.), and where 55.3 pmol/L or higher PTHrP is detected in measuring PTHrP-C terminus (for example, SRL, Inc.) are included in the situation. Further, the term includes the case where 55.3 pmol/L or higher, preferably 100 pmol/L or higher, more preferably 300 pmol/L or higher, yet more preferably 499 pmol/L or higher PTHrP is detected when measuring PTHrP (C-terminus) in cell culture supernatant according to the method described in the Examples below. In the present invention, human SCLC cell line can be used as particularly suitable cells. Although the human SCLC cell lines SBC-3 and SBC-5 cells which are preferably used were kindly provided by Dr. K. Hiraki (Okayama University, Okayama, Japan), they can also be commercially available from Human Science Research Resources Bank (Osaka, Japan). The multi-drug resistant SCLC cell line SBC-3/ADM was established as previously reported (Nakamura, K. et al., Cancer Res. 59:5323-5330, 1999). The human lung squamous cell carcinoma RERF-LC-AI cells were kindly provided by Dr. Akiyama (Radiation Effects Research Foundation, Hiroshima, Japan), but they can also be commercially available from RIKEN Cell Bank (Ibaragi, Japan). The human lung adenocarcinoma PC-14 cells, human SCLC cells H69 and its etoposide-resistant variant, H69/VP, were kindly provided by Dr. N. Saijo (National Cancer Center, Tokyo, Japan). The human lung adenocarcinoma PC-14 cells can also be commercially available from RIKEN Cell Bank (Ibaragi, Japan), and human SCLC cells H69 are commercially available from ATCC (American Type Culture Collection).

The method for culturing tumor cells may be any methods commonly used in the art, and is not particularly limited. For example, SBC-3, SBC-3/ADM and SBC-5 cells can be maintained in Eagle MEM supplemented with 10% heat-inactivated fetal bovine serum (GIBCO, Grand Island, N.Y.) and gentamicin (Schering-Plough, Osaka, Japan) and 4 mM HEPES. The RERF-LC-AI, PC-14, H69 and H69/VP cells can be maintained in RPMI 1640 supplemented with 10% heat-inactivated fetal bovine scrum (CRPMI 1640) and gentamicin. All cell lines are preferably incubated at 37° C. in a humidified atmosphere of 5% $CO_2$ in air.

Cells for implanting into animals can be prepared as follows. Tumor cells harvested are washed, for example, with $Ca^{2+}$-and $Mg^{2+}$-free phosphate buffered saline (CMF-PBS). Cell viability can be determined by trypan blue exclusion test, and only single cell suspensions of >90% viability are preferably used.

In the present invention, non-human animals include vertebrate, specifically mammals such as mouse, rat, hamster, guinea pig, rabbit, pig, miniature pig, sheep, cat, and dog, birds such as chicken, and fishes, but any animals other than human are included without any restriction. Animals which belong to rodents, for example, mouse, rat, hamster, and the like, are preferably used in the present invention, and mouse is most preferably used, due to the ease of breeding and manipulation. Any kinds of mouse which are used in the art can be suitably used. For example, Male CB-17/Icr-scid mice, ages 6-8 weeks, can be obtained from Charles River Japan, Inc. (Yokohama, Japan) and maintained under specific pathogen-free conditions throughout the experiment.

The bone metastasis model animal of the present invention can be produced from normal animals. However, more suitable results can be obtained where immunodeficient animals are used. Immunodeficient animals may be obtained or produced by way of known means in the art For example, SCID mouse can be commercially available from CLEA Japan Inc. (Tokyo, Japan) or Charles River Japan Inc. (Yokohama, Japan).

The term "peripheral administration" means herein parenteral administration route by which agents are administered directly into the body, and includes intravenous, intramuscle, intracutaneous, subcutaneous, and intraperitoneal administrations, and does not include percutaneous, inhalation, intracerebral, and ophthalmic administrations.

The bone metastasis model animal of the present invention can be produced, for example, according a process comprising following steps:

(i) The Step of Providing a Non Human Animal Having Reduced Immunity

When implanting heterologous (tumor) cells into animals, it is necessary to reduce host immunity. Generally, nude mouse which is deficient of T cell function due to lack of thymus, or SCID mouse which is deficient of B cell function as well as T cell function, is used as a immunodeficient model for implanting tumor. However, NK cell functions in these models, and NK cell inactivation is required in order to assure a good take of tumor. In that case, asialo-GM1 antibody or TMβ1 treatment employed herein is preferably used. Another method may be that of producing immuno-suppressed mouse by irradiating X-ray to the whole body of a mouse.

Immunodeficient animal of the present invention includes commonly available nude mouse, SCID mouse, a mouse obtained by administration of asialo-GM1 antibody or TMβ1 into nude mouse or SCID mouse, and X-ray irradiated mouse, and the like.

In order to facilitate the metastasis of human lung cancer cell lines, natural killer (NK) cells may preferably be depleted in SCID mice. The depletion of NK cells may be carried out, for example, by treatment of SCID mice with anti-IL-2 receptor antibody, especially anti-IL-2 receptor β-chain antibody (TMβ1). Antibody can be derived from any kinds of animals including human, and mouse antibody is particularly preferable. Although anti-mouse IL-2 receptor βchain monoclonal Ab, TM-β1 (IgG2b), was kindly supplied by Drs. M. Miyasaka and T. Tanaka (Osaka University, Osaka, Japan), it can be produced according to the method described in Japanese Patent No.3040451 (Tanaka, T. et al., J. Exp. Med. 178 1103-1107, 1993). For example, TM-β1 Ab (1 mg/1 ml PBS/mouse) may be injected ip. into SCID mice 2 days before tumor inoculation (Yano, S. et al., Int. J. Cancer 67:211-217, 1996).

(ii) The Step of Introducing Tumor Cells Capable of Inducing Bone Metastasis Into the Non-human Animal By Peripheral Administration Introduction of tumor cells by administration can be carried out, preferably by injection, more preferably by intravenous injection. Injection may be performed with 0.3 ml of tumor cells (approximately $1-5 \times 10^6$) into the lateral tail vein of unanesthetized SCID mice pretreated with TM-β1 Ab. After the indicated periods, bone metastasis can be evaluated by X-ray photography (Fuji Film, Tokyo, Japan). To determine the visceral metastases, the mice are sacrificed and the number of metastatic foci on the lungs, liver, kidneys and lymph nodes are counted macroscopically.

For histo-pathological study, the major organs of the animal harvested may be fixed in 10% phosphate-buffered formalin, sectioned and stained with hematoxylin and eosin by standard procedure.

The present invention also provides a method for evaluating efficiencies of treatment against bone metastasis of tumor cells, comprising the step of:

(i) applying a treatment to the non-human bone metastasis model animal according to any one of claims 1 to 9; and (ii) comparing the size and/or extent of bone metastasis, and/or symptoms resulted from bone metastasis, with control animal.

The term "treatment" includes treatment by some agents and radiotherapy, and also includes prevention (inhibition of enlargement) of bone metastasis. When a treatment is effective, contraction or disappearance, or inhibition of enlargement of bone metastasis can be observed, and relief of some symptoms resulted from bone metastasis, such as paralysis, can also be observed. The term "control animal" means an animal under the same condition as the animal applied the treatment, except for without the treatment. Alternatively, the control animal may be the same animal before the treatment.

Further, the present invention provides use of the non-human bone metastasis model animal according to claim to any one of claims 1 to 9 for determining the effect of a test substance on bone metastasis, comprising the steps of:

(i) administering the test substance to the animal; and (ii) comparing the size and/or extent of bone metastasis, and/or symptoms resulted from bone metastasis, with control animal.

In the present specification, test substance is not particularly limited, and include, for example, peptides, proteins, non-peptide compounds, synthetic compounds, fermentation products, cell extract, various factors in cells. The administration of test substance can be carried out by oral or parenteral administration which are known in the art such as intravenous injection, subcutaneous injection, and the like, and the route of administration can be appropriately selected depending on animals used, the degrees of bone metastasis, and the like. Alternatively, normal condition can be the condition of administration of a specified factor in cells, by removing the factor from the cells or reducing the function of the factor. The term "control animal" means herein an animal under the same condition as the animal administered with test substance, except for without the administration. Alternatively, the control animal may be the same animal before the administration. The use of the bone metastasis model animal according to the present invention allows a simple evaluation of whether the test substance is effective or not.

As described above, we established a novel bone metastasis model animal by iv injection of tumor cells. Mice with multiple bone metastases showed neurological disorders (paraplesia or monoplesia of hind leg) and hypercalcemia, which are frequently observed in lung cancer patients with bone metastases, suggesting that our bone metastasis model seems to reproduce the characteristics of bone metastasis of lung cancer in humans.

The advantage of our model over prior art are 1) the incidence of bone metastases is 100%, 2) the procedure involved is easy, though immunodeficient animal is preferable to facilitate metastasis formation, 3) since visceral metastasis is also reproducibly developed, antimetastatic effect of drags in various organs can be evaluated in one model.

The formation of bone metastasis consists of several steps, including tumor-cell arrest at capillaries in bone marrow, extravasation, tumor-cell invasion with bone resorption, and tumor growth. Therefore, various cytokines that modulate these steps can facilitate bone metastasis formation. Pro-inflammatory cytokines (IL-1, IL-6, TNF-α) up-regulate bone resorption and expression of adhesion molecules expressed on the capillaries, and pro-angiogenic cytokines (VEGF and IL-8) can stimulate angiogenesis. In addition, M-CSF and IL-10 can activate macrophages and lymphocytes, respectively, can inhibit tumor growth (28-29). Nevertheless, there was no correlation between the expression of these cytokines in human lung cancer cells used and the formation of bone metastasis.

Recently, it was reported that PTHrP-expression in primary tumors directly correlated with the incidence of bone metastasis in breast cancer patients Powell, G. J. et al., Cancer Res. 51:3059-3061, 1991). In addition, the high level of PTHrP expression was detected in the bone metastases in the patients with breast or prostate cancer (Bundred, N. J. et al., Eur. J. Cancer 28:690-692, 1992; Bouizar, Z. et al., Cancer Res. 53:5076-5078, 1993). Consistent with these reports, highly PTHrP expressing cells had highest potential to produce bone metastasis in NK-cell depleted SCID mice. Therefore. PTHrP, which stimulates bone resorption, may play a crucial role on developing bone metastasis in our model.

Hypercalcemia is frequently observed in lung cancer patients. It can be caused by two different mechanisms, namely HHM and LOH (local osteolytic hypercalcemia) (Burtis, W. J. et al., N. Engl. J. Med. 322:1106-12, 1990). HHM is mediated via PTHrP produced by tumor cells. Since PTHrP indirectly stimulates bone resorption by osteoclasts and augments resorption of calcium in the kidneys, the calcium level in the serum is elevated. In LOH locally produced cytokines (IL-1, IL-6, TNF-α) by tumor cells promote proliferation and differentiation of osteoclast-linage cells, induced bone resorption, and hence cause hypercalcemia (Mundy, G. R., Bone, 12(supple) S1-S6, 1991; Yoneda, T., M. Noda(ed.), Cellular and molecular biology of bone, 375-412, New York, Academic Press, 1993; Jilka, R L. et al., Science 257:88-91, 1992; Roodman, G. D., Calcif. Tissue Int. 53, S94-S98, 1993; Tamura, T. et al., Proc. Natl. Acad. Sci. USA 90:11924-11928, 1993; Kurihara, N. et al., J. Immunology 144:4226-4230, 1990; Tashjian, Jr A. H. et al., Proc. Natl. Acad. Sci USA 82:4535-4538, 1985; Oreffo, R. O. et al., Biochem. Biophys. Res. Commun. 158:817-823, 1989). In the present study, hypercalcemia was observed in SBC-5cell inoculated SCID mice in a time-dependent manner. Tumor cells highly expressed PTHrP at both protein and mRA levels, whereas no IL-1, IL-6, or TNF-α was detected in the culture supernatants of the cells, suggesting that hypercalcemia observed in mice inoculated with these cells may be due to PTHrP produced by these cells (HHM mechanism).

Interesting was the present finding that paralysis, a sign caused by bone metastasis, happened in all the mice inoculated with SBC-5 cells. Nevertheless, the paralysis was also observed at lower incidence (10-60%) in mice with bearing SBC-3, SBC-3/ADM, H69, or H69/VP, but the radiolucent lesions (a hallmark of osteolytic bone metastasis) could not be detected on X-ray photograph, suggesting that metastases to the brain or spinal cord might be involved in these mice.

The formation of multi-organ metastasis is critical problem in the management of lung cancer patients. In this study, all 8 human lung cancer cell lines tested developed multiple organ metastases in NK-cell depleted SCID mice. Interestingly, two adenocarcinoma cell lines produced metastases mainly in the lungs, whereas five small cell carcinoma cell lines formed lesions mainly in the liver, kidneys and systemic lymph nodes, resembling their clinical behavior. Although we examined the expression of various cytokines in these cell lines to identify key molecules responsible for organ specific metastasis, no correlation was observed between cytokine expression and metastatic potential. Of 8 cell lines tested, SBC-5, overexpressing PTHrP, most aggressively produced metastases into multiple visceral organs (such as the lungs, liver, kidneys and systemic lymph nodes) in addition to bone metastasis. Recent report showed that PTHrP-gene transfection to human prostate cancer cells resulted in resistant to apoptotic stimuli and facilitating tumor growth in vivo (Dougherty, M. K. et al., Cancer Res. 59:6015-6022 1999).

depleted SCID mice. NK-cell depleted SCID mice were inoculated i.v. through tail vein into the mice with $1\text{-}5\times10^6$ tumor cells, and were sacrificed on the day after the indicated periods, and the number of metastatic colonies into the lungs, livers, kidneys and lymph nodes were counted. All recipient mice developed tumor lesion and many of the mice became morbid by the time of sacrifice (Table 1).

TABLE 1

Pattern of Metastasis Produced by Human Lung Cancer Cell Lines in NK-Cell Depleted SCID Mice

| Cell line | Day of Sacrifice | Number of Metastasis; median (Range) | | | | |
|---|---|---|---|---|---|---|
| | | Bone | Lungs | Liver | Kidneys | Lymph Nodes |
| Squamous cell carcinoma | | | | | | |
| RERF-LC-AI[a] | day 42 | All 0 | All 0 | 67(38->100) | 19(15-30) | 4(0-18) |
| Adenocarcinoma | | | | | | |
| PC-14[a] | day 28 | All 0 | >100 | 3(1-7) | 5(3-13) | 1(0-3) |
| A549[a] | day 56 | All 0 | >100 | 1(0-2) | All 0 | 10(4-14) |
| small cell carcinoma | | | | | | |
| SBC-5[a] | day 35 | 6(4-9) | 31(9-38) | 58(32-84) | 6(3-20) | 3(1-4) |
| SBC-3[a] | day 42 | All 0 | All 0 | 12(7-21) | 12(10-17) | 13(6-22) |
| SBC-3/ADM[a] | day 35 | All 0 | All 0 | 54(41-58) | 1(0-2) | 4(2-7) |
| H69[b] | day 56 | All 0 | All 0 | 2(1-3) | 6(2-12) | 32(23-43) |
| H69/VP[b] | day 56 | All 0 | All 0 | 15(9-16) | 19(17-25) | 21(10-28) |

[a] $1 \times 10^6$ cells were injected.
[b] $5 \times 10^6$ cells were injected.

Therefore, PTHrP might facilitate the metastasis formation of SBC-5 cells not only to the bone but also to visceral organs.

In summary, we established the model for bone metastasis with dissemination by intravenous injection with tumor cells. Our model resembles characteristics of small cell lung cancer in humans, because tumor cells produced multi-organ metastasis with osteolytic bone leasions causing paralysis and induced hypercalcemia in recipient mice. In addition, our data suggest that PTHrP secreted by tumor cells plays a crucial role in the process of bone metastasis and hypercalcemia. Therefore, our bone metastasis model may be useful for understanding the biology of bone metastasis and developing novel therapeutic strategies for lung cancer patient with multi-organ metastases, including bone metastasis.

EXAMPLES

The present invention is further described in detail hereafter referring to Examples. However, it is intended that the present invention should not limited in these Examples. Moreover, none of materials used in the experiments contained endotoxins, as judged by the limulus amebocyte assay (Seikagaku Kogyo, Tokyo, Japan: minimum detection level, 0.1 ng/ml).

Example 1

Pattern of Metastasis Produced by Human Lung Cancer Cell Lines in NK-cell Depleted SCID Mice We examined the pattern of multi-organ metastasis produced by 8 different human lung cancer cell lines in NK-cell Squamous cell carcinoma (RERF-LC-AI) cells produced metastatic colonies mainly in the liver and kidneys. Adenocarcinoma PC-14 and A549 cells formed metastases mainly in the lungs. Four out of 5 small cell carcinoma cell lines (SBC-3, SBC-3/ADM, H69 and H69/VP) developed metastases mainly in the liver, kidneys and systemic lymph nodes. Among these cell lines, only one cell line of small cell lung cancer (SBC-5) developed metastatic colonies in bones as well as other organs such as lungs, liver, kidneys and systemic lymph nodes. Paralysis (paraplesia and monoplesia in the hind leg) was occasionally observed in the recipient mice bearing bone metastasis of SBC-5.

Example 2

X-ray and Histological Analysis of Bone Metastasis Produced by SBC-5 Cells

Bone metastases obtained in Example 1 were determined by X-ray photography. Multiple bone metastases were reproducibly developed in the mice injected iv with SBC-5 cells and bone metastasis lesions were detected as radiolucent lesions on X-ray photograph (FIG. 1A), indicating osteolytic bone metastases mainly in the spine (FIG. 1B) and bone of extremities (FIG. 1C). Histological analysis show that these lesions consist of tumor cells with multi-nucleated cells (FIGS. 2A and B). The mice with these lesions had paralysis of hind legs and urinary retention with enlarged bladder, probably due to pathological fracture and/or compression of spinal cord caused by bone metastasis.

Example 3

Effect of Tumor-cell Number on Bone Metastasis in NK-cell Depleted SCID Mice To determine the optimal experimental conditions for bone metastasis, we injected various numbers of SBC-5 cells into NK-cell depleted SCID nice. When the mice became moribund, the mice were sacrificed and the number of bone metastasis was determined by X-ray photograph. The number of visceral organs was determined macroscopically. The number of bone metastases, as well as visceral metastases, depended on the number of cells injected (Table 2). Based on these results, $1 \times 10^6$ SBC-5 cells were injected in subsequent experiments.

TABLE 4

The Kinetics of Body Weight and Levels of Calcium and PTHrP of NK-Cell Depleted SCID Mice Injected with SBC-5 Cells

| Days of Sacrifice | Body Weight(g) Med. | Range | Ca (mg/dl) Med. | Range | PTHrP (pmol/l) Med. | Range |
|---|---|---|---|---|---|---|
| 10 | 21.57 | 20.1-23.8 | 8.0 | 8.0-8.2 | 24.1 | <10.0-63.2 |
| 14 | 22.50 | 21.2-23.8 | 9.2 | 9.0-10.4 | 88.2 | 26.3-143 |
| 21 | 21.92 | 21.7-26.0 | 9.6 | 9.2-10.5 | 95.3 | <10.0-115 |
| 28 | 18.64 | 16.6-21.3 | 9.9 | 9.0-10.2 | 299.0 | 146-527 |
| 35 | 16.00 | 13.3-18.4 | 12.0 | 9.5-15.0 | 544.3 | 317-1020 |

TABLE 2

Pattern of Multiple Organ Metastases Produced by SBC-5 Cells in NK-Cell Depleted SCID Mice

| Number of Injection | Days of Sacrifice | Bone Inc.[a] | Med[b] | Range | Lungs Inc. | Med[b] | Range | Liver Inc. | Med[b] | Range | Kidneys Inc. | Med[b] | Range | Lymph Nodes Inc. | Med[b] | Range |
|---|---|---|---|---|---|---|---|---|---|---|---|---|---|---|---|---|
| $1 \times 10^5$ | 121 | 3/5 | 3 | 0-6 | 0/5 | 0 | All 0 | 5/5 | 30 | 7-45 | 0/5 | 0 | All 0 | 2/5 | 3 | 0-5 |
| $5 \times 10^5$ | 49 | 5/5 | 6 | 1-8 | 2/5 | 3 | 0-10 | 5/5 | 25 | 14-50 | 3/5 | 2 | 0-4 | 3/5 | 2 | 0-3 |
| $1 \times 10^6$ | 35 | 5/5 | 4 | 2-5 | 5/5 | 5 | 3-18 | 5/5 | 47 | 25-58 | 5/5 | 2 | 1-3 | 5/5 | 2 | 1-3 |
| $2 \times 10^6$ | 35 | 5/5 | 4 | 3-6 | 5/5 | 11 | 9-24 | 5/5 | 49 | 33-84 | 5/5 | 9 | 7-10 | 5/5 | 3 | 2-5 |

[a]Inc., incidence;
[b]Med., median.

Example 4

Time Kinetics of Bone and Visceral Metastases Produced by SBC-5 Cells

We next explored the kinetics of bone metastasis formation by SBC-5 cells. Twenty-five SCID mice depleted of NK cells were intravenously injected with $1 \times 10^6$ SBC-5 cells, and the formation of bone metastasis was examined by X-ray photography on days 10, 14, 21, 28 and 35. Four to five mice were sacrificed at each point to determined visceral organ metastasis. Bone metastasis was detected as early as on day 28 and was observed in all recipient mice on day 35 (Table 3). Consistent with bone metastasis formation, loss of body weight was observed as early as on day 28 (Table 4). On the other hand, metastases to the lung and liver were developed by day 21, and metastases to the kidneys and lymph nodes were produced by day 28. On day 35, all mice developed metastatic lesions into multiple organs, such as the lungs, liver, kidneys and lymph nodes.

The level of calcium in the mouse serum was determined using methylxylenol blue as a substrate for luminescence (Ohtsuka Pharmaceutical Co., Tokushima, Japan).

Example 5

Expression PTHrP and Metastasis-related Molecules in Human Lung Cancer Cell Lines

TABLE 3

Time Kinetics of Multiple Organ Metastases Produced by SBC-5 Cells in NK-Cell Depleted SCID Mice

| Days of Sacrifice | Bone Inc.[a] | Med[b] | Range | Lungs Inc. | Med | Range | Liver Inc. | Med | Range | Kidneys Inc. | Med | Range | Lymph Nodes Inc. | Med | Range |
|---|---|---|---|---|---|---|---|---|---|---|---|---|---|---|---|
| 10 | 0/25 | 0 | All 0 | 0/4 | 0 | All 0 | 0/4 | 0 | All 0 | 0/4 | 0 | All 0 | 0/4 | 0 | All 0 |
| 14 | 0/21 | 0 | All 0 | 0/4 | 0 | All 0 | 0/4 | 0 | All 0 | 0/4 | 0 | All 0 | 0/4 | 0 | All 0 |
| 21 | 0/17 | 0 | All 0 | 4/4 | 18 | 1-21 | 4/4 | 6 | 5-8 | 0/4 | 0 | All 0 | 0/4 | 0 | All 0 |
| 28 | 8/13 | 2 | 0-4 | 5/5 | 17 | 8-34 | 5/5 | 57 | 34-87 | 5/5 | 5 | 3-13 | 2/5 | 1 | 0-2 |
| 35 | 8/8 | 6 | 4-9 | 8/8 | 31 | 9-38 | 8/8 | 58 | 32-84 | 8/8 | 6 | 3-20 | 8/8 | 3 | 1-4 |

[a]Inc., incidence;
[b]Med., median.

PTHrP and IL-11 are reported to play a crucial role in bone resorption and bone metastasis (20-27). We determined whether expression of PTHrP and IL-11 in the human lung cancer cell lines correlated with their potential to produce bone metastasis. Tumor cells ($5 \times 10^5$) cells were incubated in CRPMI1640 for 24 hr, and the supernatants were harvested. The level of PTHrP in culture supernatants and mouse serum can be determined using a radioimmuno assay (Ohtsuka Pharmaceutical Co., Tokushima, Japan). The levels of cytokines (VEGF, IL-6, IL-8, IL-10, M-CSF) in the culture supernatants were measured by ELISA (Ohtsuka Pharmaceutical Co. Tokushima, Japan).

Polymerase chain reaction OCR) analysis was carried out as follows. First-strand cDNA was synthesized from 1 μg total RNA using a RNA LA PCR Kit (Takara, Tokyo, Japan) in 20 μl of reaction mixture, according to the manufacture's instructions. The synthesized first-strand cDNA (20 μl) was amplified by polymerase chain reaction (PCR) in a final volume of 100 μl containing 1×LA PCR Buffer II, 2.5 mM $MgCl_2$, 20 pmol of each primer, and 2.5 U of TaKaRa LA Taq polymerase RNA LA PCR Kit (Takara, Tokyo, Japan). Sequences of PTHrP primers used were sense 5'-ATG CAG CGG AGA GAC TGG TTC AG-3' (SEQ ID NO: 1) and antisense 5'-TCA ATG CCT CCG TGA ATC GAG CTC CAG AGC CGT-3' (SEQ ID NO: 2) (Walsh, C. A. et al., Bone and Mineral 27 43-50, 1994). PCR amplification of PTHrP cDNA was performed under the following conditions: 30 cycles, 30 sec at 94° C., 30 sec at 58° C., 30 sec at 72° C. Before the first cycle, a denaturation 2 min at 94° C. was included, and after 30 cycles the extension was prolonged for 7 min at 72° C. (Walsh, C. A. et al., Bone and Mineral 27 43-50, 1994). Sequences of IL-11 primers used were sense 5'-ACT GCT GCT GCT GAA GAC TCG GCT GTG A-3' (SEQ ID NO: 3) and antisense 5'-ATG GGG AAG AGC CAG GGC AGA AGT CTG T-3' (SEQ ID NO: 4) (Auernhammer, C. J. and Melmed, S., Endocrinology 140:1559-1566, 1999). PCR amplification of IL-11 cDNA was performed under the following conditions: 40 cycles, 30 sec at 94° C., 30 sec at 58° C., 45 sec at 72° C. Before the first cycle, a denaturation step for min at 94° C. was included, and after 30 cycles the extension was prolonged for 3 min at 72° C. (Auernhammer, C. J. and Melmed, S., Endocrinology 140:1559-1566, 1999). PCR products were analyzed by 1.5% agarose gel electrophoresis and visualized by ethidium bromide staining with UV light.

As a result, all the eight cell lines tested expressed IL-11 mRNA, but there was no discernible differences in IL-11 mRNA expression among 8 cell lines (FIG. 3). On the other hand, 6 out of 8 cell lines expressed PTHrP mRNA and the strongest expression was observed in SBC-5 cells. Consistent with mRNA expression, SBC-5 cells secreted more than 10 times higher levels of PTHrP protein compared to other cell lines (Table 5), indicating direct association of the expression of PTHrP and bone metastasis in human lung cancer cells.

TABLE 5

Cytokine Production by Human Lung Cancer Cell Lines

|  | PTHrP[a] | VEGF[b] | IL-6[b] | IL-8[b] | M-CSF[b] | IL-10[b] |
|---|---|---|---|---|---|---|
| RERF-LC-AI | <10 | 1142 | 67 | 1025 | 454 | <20 |
| PC-14 | 15.1 | 11429 | 106 | 236 | 911 | <20 |
| A549 | 30.8 | 743 | <20 | 576 | 89 | <20 |
| SBC-5 | 499 | 2040 | <20 | <20 | <20 | <20 |
| SBC-3 | 19.6 | 1106 | <20 | 13061 | 297 | <20 |
| SBC-3/ADM | 14.4 | 1591 | <20 | 16502 | 310 | <20 |
| H69 | <10 | 3344 | <20 | <20 | <20 | <20 |
| H69/VP | <10 | 3273 | <20 | <20 | <20 | <20 |

[a] 10 pmol/L
[b] pg

Data shown are the representation of three sets of independent experiments.

Example 6

Levels of PTHrP and Calcium in the Serum of SBC-5 Cell-bearing Mice

PTHrP has been reported to be responsible for hypercalcemia in HHM. We evaluated the levels of PTHrP and calcium in the serum of SBC-5 cell bearing mice. The levels of serum calcium and PTHrP were increased in a time-dependent manner, indicating direct correlation of bone metastasis (or tumor burden) and levels of these markers and loss of body weight (Table 4). These phenomena reflect clinical patients of human lung cancer with bone metastasis.

Example 7

Abilities of Lung Cancer Cells to Produce Cytokines Related to Bone Metastasis

We also examined abilities of lung cancer cells to produce bone metastasis-related cytokine such as IL-1α, IL-6, TNF-α, IL-10, M-CSF, VEGF and IL-8. Although 8 cell lines secreted various levels of these cytokines (Table 5), there was no correlation between the expression level of these cytokines and formation of bone metastasis.

All publication, patents and patent application cited herein are incorporated herein by reference in their entirety.

The invention claimed is:

1. A bone metastasis model mouse exhibiting bone metastasis of tumor cells, wherein a suspension comprising single cells of human small cell lung carcinoma SBC-5 cells has been introduced by intravenous administration, wherein the mouse is immunodeficient, and wherein the metastasis occurs in the mouse's own bone.

2. The bone metastasis model mouse according to claim 1, wherein the mouse exhibits multi-organ metastasis of tumor cells.

3. The bone metastasis model mouse according to claim 2, wherein the multi-organ metastases include metastases to one or more organs selected from lung, liver, kidney, and lymph node.

4. The bone metastasis model mouse according to claim 1, wherein the mouse is a SCID mouse.

5. A method for producing a mouse exhibiting bone metastasis of tumor cells, comprising:
   (i) providing an immunodeficient mouse; and
   (ii) introducing a suspension comprising single cells of human small cell lung carcinoma SBC-5 cells into the mouse by intravenous administration, wherein the metastasis occurs in the mouse's own bone.

6. The method according to claim 5, wherein the immunodeficient mouse is produced by inactivating NK cells in the mouse.

7. The method according to claim 5, wherein the immunodeficient mouse is produced by reducing the number of NK cells in the mouse.

8. The method according to claim 5, wherein the immunodeficient mouse is produced by depleting NK cells in the mouse.

9. The method according to claim 5, wherein the immunodeficient mouse is produced by administering an anti-IL-2 receptor antibody to the mouse.

10. The method according to claim 9, wherein the antibody is anti-IL-2 receptor β-chain antibody.

11. The method according to claim 9, wherein the antibody is derived from a mouse.

12. The method according to claim 5, wherein the immunodeficient mouse is a SCID mouse.

13. A method for determining the effect of a test substance on bone metastasis, comprising:
    administering the test substance to a subject bone metastasis model mouse according to claim 2 or claim 3; and
    comparing the size and/or extent of bone metastasis, and/or symptoms resulting from bone metastasis, of the subject mouse with that of a control bone metastasis model mouse, wherein the test substance was not administered to the control mouse, and wherein differences between the subject mouse and the control mouse indicate the efficiency of the treatment;
    thereby determining the effect of the test substance on bone metastasis.

* * * * *

UNITED STATES PATENT AND TRADEMARK OFFICE
CERTIFICATE OF CORRECTION

PATENT NO. : 7,402,727 B2  
APPLICATION NO. : 11/120508  
DATED : July 22, 2008  
INVENTOR(S) : Sone et al.

It is certified that error appears in the above-identified patent and that said Letters Patent is hereby corrected as shown below:

On the title page, the Terminal Disclaimer information has been omitted. Item (45) and the Notice information should read as follows:

-- (45) **Date of Patent: * Jul. 22, 2008**

(*)    Notice: Subject to any disclaimer, the term of this patent is extended or adjusted under 35 U.S.C. 154(b) by 15 days.

This patent is subject to a terminal disclaimer. --

Signed and Sealed this

Sixteenth Day of September, 2008

JON W. DUDAS  
*Director of the United States Patent and Trademark Office*